US011346825B2

(12) United States Patent
Tatineni et al.

(10) Patent No.: US 11,346,825 B2
(45) Date of Patent: May 31, 2022

(54) ARSENIC ANALYSIS

(71) Applicants: Balaji Tatineni, Fort Mill, SC (US); Ivars Jaunakais, Charlotte, NC (US)

(72) Inventors: Balaji Tatineni, Fort Mill, SC (US); Ivars Jaunakais, Charlotte, NC (US)

(73) Assignee: INDUSTRIAL TEST SYSTEMS, INC., Rock Hill, SC (US)

( * ) Notice: Subject to any disclaimer, the term of this patent is extended or adjusted under 35 U.S.C. 154(b) by 204 days.

(21) Appl. No.: 16/588,240

(22) Filed: Sep. 30, 2019

(65) Prior Publication Data
US 2021/0096112 A1 Apr. 1, 2021

(51) Int. Cl.
*G01N 31/00* (2006.01)
*G01N 33/18* (2006.01)

(52) U.S. Cl.
CPC .......... *G01N 31/005* (2013.01); *G01N 33/18* (2013.01)

(58) Field of Classification Search
CPC .................................................. G01N 33/18
USPC ........... 436/73, 164, 166, 174–175, 181–182
See application file for complete search history.

(56) References Cited

U.S. PATENT DOCUMENTS

| | | | | | |
|---|---|---|---|---|---|
| 3,243,377 | A | * | 3/1966 | Stolar | A61K 8/22 510/100 |
| 3,601,321 | A | * | 8/1971 | Barth | A61K 8/0225 241/3 |
| 3,697,227 | A | * | 10/1972 | Goldstein | B01L 3/502 422/409 |
| 3,741,727 | A | * | 6/1973 | Stroterhoff | B01L 3/5082 436/182 |
| 3,843,545 | A | * | 10/1974 | Heusten | C02F 1/766 252/181 |
| 3,968,048 | A | * | 7/1976 | Bolan | C09G 1/14 510/196 |
| 3,997,459 | A | * | 12/1976 | Bogie | A61K 8/22 510/116 |
| 4,216,104 | A | * | 8/1980 | Gergely | A47K 7/03 15/104.93 |
| 4,272,393 | A | * | 6/1981 | Gergely | A47K 7/03 134/2 |
| 4,822,512 | A | * | 4/1989 | Auchincloss | A01N 59/00 424/613 |
| 5,266,121 | A | * | 11/1993 | Cioletti | C11D 3/168 134/22.19 |
| 5,660,821 | A | * | 8/1997 | Birbara | A01N 25/34 424/76.7 |
| 6,008,171 | A | * | 12/1999 | Hughes | A61K 8/22 424/44 |
| 6,171,552 | B1 | * | 1/2001 | Takeya | G01N 1/34 422/68.1 |
| 6,197,201 | B1 | | 3/2001 | Misra et al. | |
| 6,696,300 | B1 | | 2/2004 | Jaunakais | |
| 2002/0000414 | A1 | * | 1/2002 | Kroll | G01N 31/22 210/752 |
| 2002/0108910 | A1 | * | 8/2002 | Lyon | C02F 1/70 210/719 |
| 2004/0002433 | A1 | * | 1/2004 | Buckland | A01N 59/02 510/302 |
| 2004/0086425 | A1 | * | 5/2004 | Jaunakais | G01N 1/2273 422/86 |
| 2006/0205626 | A1 | * | 9/2006 | Gant | A01N 59/26 510/367 |
| 2007/0015673 | A1 | * | 1/2007 | Davis | C11D 7/12 510/218 |
| 2007/0031914 | A1 | * | 2/2007 | Zhu | C12Q 1/6883 435/25 |
| 2008/0045593 | A1 | * | 2/2008 | Kaiser | A62D 3/38 514/557 |
| 2008/0069728 | A1 | * | 3/2008 | Attar | G01N 31/22 422/400 |
| 2010/0155330 | A1 | | 6/2010 | Burba et al. | |
| 2011/0020943 | A1 | * | 1/2011 | Okamoto | G01N 21/78 436/73 |
| 2015/0000700 | A1 | * | 1/2015 | Coxon | B08B 3/08 134/7 |
| 2017/0299502 | A1 | * | 10/2017 | Schanzer | G01N 33/1813 |
| 2017/0340549 | A1 | * | 11/2017 | Anderheggen | A61K 8/19 |

OTHER PUBLICATIONS

Anderson, R. K. et al., Analyst 1986, 111, 1143-1152.*
Rude, T. R. et al, Fresenius' Journal of Aalytical Chemistry 1994, 350, 44-48.*
Cherukuri, J. et al, International Journal of Environmental Research and Public Health 2005, 2, 322-327.*
Hashem, M. A. et al, Analytical Sciences 2011, 27, 733-738.*
Hu, S. et al, Journal of Environmental Sciences 2012, 24, 1341-1346.*
George, C. M. et al, Environmental Science & Technology 2012, 46, 11213-11219.*
Wilson, D., Journal of Environmental Health 2015, 78, 16-23.*
Han, D. et al, Chemical Engineering Journal 2015, 269, 425-433.*
Ghanbari, F. et al, Chemical Engineering Journal 2017, 310, 41-62.*
Hussam, A. et al, Environmental Science and Technology 1999, 33, 3686-3688.*
Kroll, D., "A visual method for the detection of arsenic", Paper Presented at the 3rd NSF International Symposium on Small Drinking Water and Wastewater Systems, Washington, DC, 2001, 4 pages.*
Kinniburgh, D. G. et al, Talanta 2002, 58, 165-180.*
Lewis, C. B., Soil and Sediment Contamination: An International Journal 2002, 11, 423-424.*
Das, J. et al, Journal of Environmental Science and Health, Part A 2014, 49, 108-115.*
Industrial Test Systems. Inc., Quick II Rapid Arsenic Test Kit instruction Booklet, Kit Part No. 431303, Nov. 7, 2017.

(Continued)

Primary Examiner — Arlen Soderquist
(74) Attorney, Agent, or Firm — Timothy R. Kroboth

(57) ABSTRACT

A simplified reagent system for the analysis of arsenic in an acidic aqueous environment is disclosed. In accordance with the inventive technology, a two reagent system is provided. The first reagent includes a combination of an acidifying agent and an oxidizing agent, and is in particulate form. The second reagent is zinc in particulate form, and is beneficially used in the analysis in the presence of an effective amount of an agent for increasing the rate of arsine gas production.

13 Claims, No Drawings

(56) References Cited

OTHER PUBLICATIONS

Industrial Test Systems, Inc., Quick Rapid Arsenic Test Kit Instruction Booklet, Kit Part No. 481396, Feb. 27, 2019.
Merck KGaA, Arsenic Test, Feb. 2013.
Merck KGaA, Arsenic Test MSDS, Jul. 26, 2013.
Tintometer GmbH, Arsenic Test, 2017.
Grainger, Arsenic Test SDS, Sep. 16, 2010.
Hach Company, Arsenic Test, 2003.
PCT /US2020/014840, International Search Report and Written Opinion of the International Searching Authority, dated May 14, 2020.

* cited by examiner

ARSENIC ANALYSIS

FIELD OF THE INVENTION

This invention relates to an analysis of arsenic that eliminates interfering oxidizable substances.

BACKGROUND OF THE INVENTION

There is a need to be able to determine the arsenic level in natural waters, drinking water and groundwater. It is also beneficial to be able to determine the arsenic level in humans, soil, pharmaceuticals, prepared biological materials and foods, and to monitor the arsenic level in certain industrial processes.

Commercially available tests for the analysis of arsenic are exemplified by tests of Industrial Test Systems, Inc., Merck KGaA, Hach Company and Tintometer GmbH, and work by the reduction of arsenic, in particular inorganic arsenic compounds such as trivalent and pentavalent arsenic compounds, in an acidic aqueous environment to arsine gas, by use of zinc as a reducing agent.

In this type of analysis, a closed reaction bottle providing a headspace above an aqueous reaction mixture, is used for the arsenic reduction reaction, and the bottle cap holds a mercuric bromide test strip in the headspace. In this way, mercuric bromide indicator is appropriately located for reaction with arsine gas, yet spaced away from the reaction mixture to avoid contact by the reaction mixture. After an appropriate reaction time, the indicator on the test strip is evaluated for color change.

In the Merck reagent system, the reagents are in powder form, and reagent 1 is sulfamic acid powder, and reagent 2 includes zinc, sodium tungstate ($\geq$1%-less than 5%) and sodium chloride.

In the Hach analysis, multiple reagents are sequentially added to an arsenic sample. The sample is adjusted to a pH of about 9, then an oxidizing agent is added to the alkaline sample to prevent sulfide interference, then EDTA is added, then the sample is acidified to a pH of about 1 using sulfamic acid powder, and then reduction of arsenic to arsine gas is carried out by the addition of powdered zinc.

A drawback of using sulfamic acid is that it is a corrosive-type acidifying agent. By the term "corrosive-type acidifying agent" as used herein, is meant an acidifying agent that causes visible destruction of, or irreversible alterations in, living tissue by chemical action at the site of contact. That type of acidifying agent is hereby differentiated in this description, from "non-corrosive type acidifying agents", which are illustrated by tartaric acid and malic acid.

In the Tintometer system, reagent 1, reagent 2 and reagent 3 are sequentially added to an arsenic sample. Reagent 1 is an aqueous permanganate solution (1-5% solution), reagent 2 is malonic acid, and reagent 3 includes zinc powder (25-50%) and sodium tungstate (1-10%).

In the Industrial Test Systems Rapid Arsenic Test Kit, reagent 1, reagent 2 and reagent 3 are in powder form, and are sequentially added to an arsenic sample. Reagent 1 is a combination of L-tartaric acid and Fe(II) and Ni(II) salts, reagent 2 is an oxidizing agent, and reagent 3 is zinc dust.

The oxidizing agent used in the reagent systems of Hach and Industrial Test Systems is Oxone®. Oxone® includes potassium peroxymonosulfate, potassium bisulfate, potassium sulfate and potassium peroxydisulfate.

Despite advances in the analysis of arsenic, there remains a significant need for a better arsenic test.

SUMMARY OF THE INVENTION

In accordance with the present invention, a simplified reagent system for arsenic analysis in an acidic aqueous reaction environment, that eliminates interference from otherwise interfering oxidizable substances, is provided. During the analysis, arsenic may be beneficially reduced to arsine gas by use of a reducing agent in the presence of an effective amount of an agent for increasing the rate of the arsine gas production.

The inventive reagent system includes a first reagent combination in particulate form. The first reagent combination beneficially includes an acidifying agent and an oxidizing agent. The acidifying agent is preferably a non-corrosive type acidifying agent. A corrosive type acidifying agent in particulate form such as sulfamic acid, is less favored for reasons that include end user safety. The first reagent combination may include combinations of acidifying agents.

The first reagent combination beneficially acidifies the reaction environment, and in the case of a sulfide-containing compound, produces non-interfering sulfate ion. Accordingly, the first reagent composition includes an oxidizing agent.

The first reagent combination beneficially contains the oxidizing agent in an amount effective, upon addition to an arsenic sample, to eliminate interference from otherwise interfering oxidizable substances. The first reagent combination may include an Fe(II) compound to enhance the elimination of interference.

The inventive reagent system also includes an arsenic reducing agent in particulate form. Beneficially, the arsenic reduction reaction is in the presence of an effective amount of an agent for increasing the rate of arsine gas production, and hence the reagent system advantageously further includes a second reagent combination in particulate form, that in combination with the reducing agent, includes at least one additive in particulate form that during the arsenic reduction reaction functions as, or from which is generated, an agent for increasing the rate of arsine gas production.

The useful additives described herein, are transition metal compounds. The second reagent combination may include combinations of useful additives.

The inventive reagent system is useful for analysis of an aqueous sample, which may be natural waters, drinking water or groundwater, or a soil extract. In addition, the inventive reagent system is useful for analysis of arsenic level in humans, and for other arsenic analyses. Thus, a urine sample may be analyzed for arsenic.

Additional advantages and beneficial features of the present invention are set forth in the detailed description, and in part will become apparent to those skilled in the art upon examination of the detailed description or may be learned by practice of the invention.

DETAILED DESCRIPTION OF THE INVENTION

In accordance with the present invention, it has been unexpectedly discovered that a reagent system for arsenic analysis in an aqueous acidic environment that eliminates interference from interfering oxidizable substances, may be simplified. Previously, it had been understood, as illustrated by the previously described prior art, that an acidifying agent and an oxidizing agent for eliminating interference by an oxidizable substance, cannot be combined for reasons of incompatibility or lack of stability, but rather must be used in the analysis in a stepwise fashion, typically with acidifying agent addition followed by oxidizing agent addition. Thus, the present invention is substantially based upon the discoveries that a combination in particulate form of certain acidifying agents and oxidizing agents may be used in an arsenic analysis that requires the elimination of interfering oxidizable substances, and in addition has the stability appropriate for commercial marketing.

Furthermore, it has been found that Fe(II) compounds may be beneficially included in the acidifying agent and oxidizing agent combination, to increase the level of oxidizable substance interference that may be eliminated, whereas Ni(II), Cu(II) and Sn(II) compounds should not be included in this reagent combination.

Based on these and other discoveries, the present invention is directed to an improved technology for the analysis of arsenic that avoids use of liquid acidifying agents such as hydrochloric acid and other corrosive type acidifying agents. Instead, the inventive reagent system uses an acidifying agent in particulate form, beneficially non-corrosive type acidifying agents, combined with an oxidizing agent in particulate form. The use of non-corrosive type acidifying agents typically benefits control of the arsenic reduction reaction whereby undesired splashing of the reaction mixture may be eliminated. Thus, better control of the arsenic reduction reaction may be achieved by the combination of a relatively safer, easier to handle acidifying agent in particulate form, with an oxidizing agent in particulate from, and as indicated by the examples, may be benefitted by use of a relatively smaller amount of the arsenic reducing agent and/or rate-benefitting additive. As a result, reproducibility of results, convenience and safety are benefitted.

In accordance with the present invention, an aqueous sample of arsenic is analyzed by the reduction of arsenic to arsine gas in an acidic aqueous reaction environment after the elimination of interfering oxidizable substances. Especially useful acidifying agents available in powder, granule or other particulate form include non-corrosive type acidifying agents such as carboxylic acids. Illustrative useful carboxylic acids include di- and tricarboxylic acids such as L-tartaric acid, malic acid, succinic acid and citric acid. If desired, more than one of these acidifying agents may be used. However, malonic acid, a dicarboxylic acid available in particulate form, is not useful when combined with a useful oxidizing agent in particulate form, in particular with Oxone® or potassium permanganate, due to lack of commercial stability of the combination. Unlike malonic acid, the above-described carboxylic acids include a C—C moiety between carboxylic acid groups.

Corrosive type acidifying agents are not intended for use by the inventive technology, and include acidifying agents in powder form such as sulfamic acid. Not only is sulfamic acid undesirable as a corrosive type acidifying agent, but also the combination in particulate form of sulfamic acid and Oxone® has been found to be not useful in analyzing an arsenic sample that includes interfering sulfide ion. However, a small amount of malonic acid in the range of about 5 to 10 wt. % or less of the amount of the acidifying agent/oxidizing agent combination, would not be expected to have a significant adverse affect on the analysis.

Beneficially the pH of the aqueous sample being analyzed, is adjusted by addition of the acidifying agent, prior to the addition of the reducing agent. The pH can then be confirmed and any further pH adjustment carried out prior to beginning the generation of arsine gas. For optimization purposes, the pH of the acidic reaction environment for the arsenic reduction reaction is beneficially in the range of about 1.8 to 2.5, and that pH range is generally achievable by using an appropriate amount of the acidifying agent/oxidizing agent combination. A pH significantly above 2.5 may result in a reduced rate of arsine gas production. A pH below 1.5 will typically not be used because of the type and amount of acidifying agent needed.

When a particular pH is targeted, a sufficient amount of the acidifying agent/oxidizing agent combination is added to the sample to attain the desired pH. The amount to be added depends upon factors including the volume of the sample, and the sample pH prior to adjusting the pH. If desired, more than one acidifying agent can be included in the reagent combination.

Salts of acidifying agents, for example carboxylic acid salts, may be included in the acidifying agent/oxidizing agent combination to adjust, or stabilize, the desired pH. Exemplary salts include alkali metal salts of useful carboxylic acids.

Because the present invention is directed to analysis of an aqueous arsenic sample that includes interfering oxidizable substances such as hydrogen sulfide, the inventive technology beneficially combines an oxidizing agent with an acidifying agent. A suitable oxidizing agent is Oxone®, a known oxidizer of hydrogen sulfide to non-interfering sulfate ion. Other reduced sulfur compounds including mercaptans, other sulfides, disulfides and sulfites, may likewise be oxidized to non-interfering sulfate ion. Other oxidizing agents in particulate form for removing interference by oxidizable substances, may be used in place of Oxone®. Illustrative are potassium peroxymonosulfate, which is an active ingredient of Oxone®, and alkali metal permanganate salts such as potassium permanganate, both of which are available in particulate form.

The acidifying agent/oxidizing agent combination includes more acidifying agent than oxidizing agent. Depending on the oxidizing agent selected, about 95 to 99.7 wt. % acidifying agent may be combined about 0.3 to 5 wt. % oxidizing agent, or about 10 to 30 wt. % oxidizing agent may be combined with about 70 to 90 wt. % acidifying agent. An about 0.3 to 5 wt. % loading of an alkali metal permanganate salt typically may be sufficient, whereas an about 10 to 30 wt. % loading of Oxone® or potassium peroxymonosulfate typically may be sufficient.

In any event, a sufficient amount of the oxidizing agent is included in the acidifying agent/oxidizing agent combination, and is beneficially added to the aqueous arsenic sample, to remove interference from otherwise interfering oxidizable substances. The amount to be added depends on factors including the sample volume, the oxidizing agent selected, and the concentration of interfering oxidizable substances in the aqueous arsenic sample. In the case of hydrogen sulfide, the acidifying agent/oxidizing agent combination beneficially includes enough oxidizing agent, such that for example, about 0.4 to 0.8 g of Oxone® or about 0.01 to 0.08 g of an alkali metal permanganate salt, may be added to the arsenic sample to remove up to about 0.5 ppm, preferably up to about 4 to 6 ppm or more, hydrogen sulfide.

As described, the aqueous sample will be acidic, for instance at a pH of about 2.3 or less, during the removal of an interfering oxidizable substance. An Fe(II) compound may be advantageously included in the acidifying agent/oxidizing agent combination to enhance the removal of interference, up to about 7 ppm or more. In this case, the acidifying agent/oxidizing agent combination may advantageously include only a very small amount of Fe(II) compound, which may range from about 0.05 to 3 wt. % of the total weight of the reagent combination, but which typically may be present in a smaller percentage than the oxidizing agent.

A useful level of iron (II) cation in the aqueous sample may range from about 5 to about 100 ppm, but will typically not be in excess of about 10 to 40 ppm. Interference with the oxidizing agent may result in the case of a concentration of iron (II) cation substantially in excess of 100 ppm. In any event, an effective level of Fe(II) cation depends upon factors including the concentration of interfering oxidizable substances in the sample, and the amount of the oxidizing agent. Thus, for example, a relatively higher concentration of an interfering oxidizable substance may require a relatively higher level of iron (II) cation.

Beneficially after addition of the acidifying agent/oxidizing agent combination or acidifying agent/oxidizing agent/Fe(II) combination to the arsenic sample, the resultant mixture may be shaken vigorously, for example, for about 15 seconds, and then allowed to stand undisturbed prior to addition of the reducing agent. A suitable reaction time for the oxidation reaction may typically range from about 2 minutes or less, to 5 minutes.

In accordance with the present invention, the inventive reagent system advantageously includes a reducing agent in powder or other particulate form. In a preferred embodiment, the reduction of arsenic, in particular of inorganic arsenic compounds such as trivalent and pentavalent arsenic compounds, to arsine gas is based upon the use of zinc as a reducing agent. However, any other suitable reducing agent for reducing arsenic in an acidic aqueous environment to arsine gas, may be used in place of zinc, provided that in a preferred embodiment, a benefit results from using an additive, hereinafter described, for increasing the rate of arsine gas production.

Generally, a relatively finer powder of the reducing agent may be preferred. In the case of zinc, zinc dust of less than 10 microns (or 325 mesh) may be particularly beneficial with a non-corrosive type acidifying agent. A useful amount of zinc for the arsenic reduction depends on factors including the concentration of arsenic in the sample. For a 100 ml sample volume, a useful amount of zinc may be in the range of about 0.2 g to Ig, and for a 250 ml sample volume may be in the range of about 0.5 to 3 g.

In accordance with the present invention, the inventive reagent system beneficially includes a combination in particulate form of the reducing agent and an additive in particulate form that during the arsenic reduction reaction functions as, or from which is generated, an agent for increasing the rate of arsine gas production. Beneficially, the reducing agent/additive reagent combination is free flowing. If desired or advantageous, the reducing agent/additive reagent combination may include an alkali metal halide such as sodium chloride.

The reducing agent/additive combination includes more reducing agent than additive, and when an alkali metal chloride is included, may include more or less of the alkali metal chloride than the amount of reducing agent. For example, about 60 to 99 wt. % reducing agent may be combined with about 40 to 1 wt. % additive. However, in the case when about 40 to 75 wt. % of an alkali metal chloride is included in the reducing agent/additive combination, the percentages of reducing agent and additive in the reagent combination are less.

The additives described herein, are transition metal compounds. Iron, cobalt, nickel, copper, tungsten, and molybdenum compounds are useful transition metal compounds. Cations of group 6 or of groups 8 to 11 (as defined by the IUPAC version of the Periodic Table) such as W, Mo, Fe, Co, Ni, and Cu may function as a rate-increasing agent. These cations are divalent transition metal cations and transition metal cations of greater valency than divalent. Useful transition metal cations include $Fe^{2+}$, $Fe^{3+}$, $Co^{2+}$, $Ni^{2+}$, $Sn^{2+}$, $Cu^{2+}$, and $W^{4+}$. In addition, a rate-increasing benefit has been found for $Sn^{2+}$ when used with tartaric acid as the acidifying agent.

A typical additive may be a salt of a useful transition metal cation, and an anion from which an acid may be derived, such as a sulfate, chloride, oxalate and acetate anion. Thus, exemplary additives are iron(II)sulfate.$7H_2O$, iron(II)chloride.$4H_2O$, iron(II)oxalate, iron(III)sulfate hydrate, cobalt(ii)acetate.$4H_2O$, nickel(II)acetate, nickel(II)sulfate.$6H_2O$, tin(II)chloride.$2H_2O$, copper(H)acetate.$H_2O$, molybdenum (V) chloride, tungsten (IV) chloride, and mixtures thereof. Other useful additives include transition metal oxides such as molybdenum (VI) oxide and tungsten (VI) oxide, and alkali metal tungsten compounds such as sodium tungstate, and alkali metal molybdenum compounds such as molybdenum tungstate. Reference is hereby made to Examples 1 to 24 of U.S. Pat. No. 6,696,300, which describe certain of these additives, and which are hereby incorporated by reference in this description.

Both hydrogen gas and arsine gas are typically produced during the arsenic reduction reaction. An effective amount of a useful agent increases the rate of arsine gas production, and the rate of arsine gas production is typically enhanced as the concentration of the agent is increased. However, other considerations may limit the useful concentration of the rate-increasing agent. For example, at or above a certain concentration, the rate of gas formation can result in splashing of the reaction mixture on the indicator pad, or the rate of formation of arsine gas can be too rapid for other reasons.

An advantageous concentration of the rate-increasing agent in the arsenic reaction mixture, may typically be about 5 to 100 ppm. However, use of a higher concentration up to about 1200 ppm, but typically not in excess of about 1500 ppm, may be useful depending upon the agent selected, the result desired, and any concentration-limiting consideration such as cost.

The concentration of the rate-increasing agent will also vary depending upon the extent to which it is desired to enhance the rate of production of arsine gas. Thus, when a particular time end point for the arsenic reduction reaction is targeted, a sufficient amount of the agent selected is used to attain sufficient arsine gas production within the time period. This amount of the rate-increasing agent will vary such that less of a relatively more effective agent is necessary, whereas more of a relatively less effective agent will be needed.

A further consideration is that certain rate-increasing agents may interfere with the oxidation reaction. For example, $Ni^{2+}$, $Co^{2+}$, and $Sn^{2+}$ cations may interfere with the oxidation reaction. Thus, it is important for the oxidation reaction to be complete before beginning the arsenic reduction reaction. Furthermore, these rate-increasing agents should be avoided as a component of the acidifying agent/oxidizing agent composition.

For a brief period of time (generally 5 to 15 seconds) immediately following the addition of the reducing agent, it will be typically beneficial to promote mixing of the resulting mixture. Beneficially, substantially complete arsenic reduction may occur within about 10 minutes. However, the time needed for the arsenic reduction reaction may be more or less, with considerations including the time needed for maximum color development from the arsenic reduction reaction.

Although the sample volume for analysis can vary, a beneficial volume will typically be in the range of 50 to 300 ml, for example, 50, 100 or 250 ml. If a low level of arsenic is suspected, it may be beneficial for a relatively larger volume to be used, for example, 250 ml instead of 100 ml. In the case of an aqueous sample of small volume, the sample may be diluted to a desired analysis volume, provided that the dilution factor is taken into account.

A suitable temperature of the aqueous sample will range between about 20° to 40° C., preferably about 25° to 30° C. A lower or higher temperature can be expected to respectively slow or increase the rate of arsenic reduction. Although a lower or higher temperature may be corrected for, it is generally recommended that the temperature of the sample be within the suitable temperature range.

Advantageously, the arsenic to arsine gas reduction reaction may be carried out in a closed reaction bottle of appropriate volume to provide a headspace above the aqueous reaction mixture, and the bottle cap is used to hold a test strip carrying a suitable indicator for arsine gas, in the headspace. Conveniently, the bottle cap may include a slit opening and the indicator may be carried by a pad on the test strip, in which case the pad is disposed in the headspace for reaction of the indicator with arsine gas, and a portion of the remainder of the test strip may extend outside the reaction bottle through the cap slit. Beneficially, the pad is sufficiently spaced away from the aqueous mixture to avoid contact by the aqueous mixture.

A suitable indicator for arsine gas is mercuric bromide. It will, of course, be understood that any other suitable indicator for arsine gas, may be used. Conveniently, the test strip or pad may be impregnated or saturated with the indicator using conventional techniques. Useful test strips are known in the prior art.

Because of relatively increased arsine gas production, sensitivity may be enhanced particularly for low levels of arsenic in the range of 0.05 ppb to about 5 or 7 ppb or more, up to about 10 ppb. The inventive test is also beneficial for higher levels of arsenic up to 50 or 100 ppb or more, even in excess of 500 ppb or more.

After the allowed time for the arsenic reduction reaction has passed, the indicator color may be conveniently visually evaluated, typically by comparison with an appropriate standardized color chart. Generally, it may be best to carry out the color comparison within about 2 minutes after the indicator has been removed from the reaction environment.

In connection with the Examples, sufficient NIST arsenic standard is added to deionized water, to give an aqueous solution having the specified concentration of arsenic. Solutions having a temperature of 20 to 28° C., are analyzed.

In these and the other examples and throughout this description, all parts and percentages are weight percent unless otherwise specified.

EXAMPLE 1

Reagent 1: A mixture of 62 g of Oxone® powder and 290 g of L-tartaric acid is prepared.

Reagent T1: A mixture of 120 g of zinc powder and 25 g of sodium tungstate is prepared. Thereafter, a portion of T1 is stored with desiccant, and a portion is stored without desiccant. The ratio of sodium tungstate to zinc powder is 1:4.8.

100 ml of an aqueous solution (deionized water) containing 5 ppb arsenic, is added to a 160 ml reaction bottle. Thereafter, 2. 7 g of Reagent 1 is added to the aqueous solution, and the mixture is capped, shaken vigorously for 15 seconds, and then the uncapped bottle is allowed to stand undisturbed for 2 minutes. Thereafter, 0.84 g of Reagent T1 (first run, mixture stored with desiccant; second run, mixture stored without desiccant) is added, and the mixture is capped and shaken vigorously for 5 seconds, and then the reaction bottle is closed using a cap that has a slit opening and holds a test strip pad carrying mercuric bromide indicator in the headspace above the aqueous reaction mixture. The concentration of tungsten ion per 100 ml is 906 ppm.

After 10 minutes, the test strip is removed and within the next 2 minutes, the pad color is visually compared with two commercially available color charts (this experiment uses Industrial Test Systems, Inc. Method 481303 and Method 481396 procedures and color charts). The results (two runs) are 5-6 ppb and 5 ppb As, respectively, and demonstrate the usefulness of a mixture of L-tartaric acid and Oxone®.

Evaluation of Stability and Removal of Sulfide Interference

Reagent 1A is a like mixture of 62 g of Oxone® powder and 290 g of L-tartaric acid. Stability of Reagent 1A is analyzed as follows:

1.33 g of Reagent 1A is dissolved in 50 ml of deionized water (resulting solution pH 1.9), and a sample of the resulting solution is evaluated using a commercially available DPD-3 test strip and Micro 20 meter (both products of Industrial Test Systems, Inc.). Conversion of KI to iodine is determined from the solution color, and the average reading (3 readings) is 127 ppm.

More than 1 year later, 1.47 g of Reagent 1A is dissolved in 50 ml of deionized water and evaluated using the same method. The average meter reading (3 readings) is 124 ppm. This result demonstrates the stability of a mixture of L-tartaric acid and Oxone® for more than 1 year.

Also more than 1 year later, Reagent 1 is evaluated for removal of sulfide interference. 2.7 g of Reagent 1 is added to 105 ml of deionized water containing 0.5 ppm sulfide ion, but 0 ppb arsenic. Concentration of sulfide ion is confirmed using Micro 20 meter sulfide procedure. The foregoing procedure of this Example is followed, and the pad color is visually evaluated to determine removal of sulfide interference using the 481396 color chart. The result is 0 ppb As, and demonstrates the removal of sulfide interference.

EXAMPLE 2

Reagent 1A is a mixture of Oxone® powder and L-tartaric acid, and corresponds to Reagent 1A of Example 1.

Reagent T2: A mixture of 45 g zinc dust, 1.57 g sodium tungstate anhydrous and 53.83 g sodium chloride is prepared. The ratio of sodium tungstate to zinc dust is about 1:28.

100 ml of deionized water containing 100 ppb arsenic, is added to a 160 ml reaction bottle. Thereafter, 2.8 g of Reagent 1A is added to the aqueous solution, and the mixture is capped, shaken vigorously for 15 seconds, and then the uncapped bottle is allowed to stand undisturbed for 2 minutes. Thereafter, 0.65 g of Reagent T2 is added, and the mixture is capped and shaken vigorously for 5 seconds, and then the reaction bottle is closed using a cap that has a slit opening and holds a test strip pad carrying mercuric bromide indicator in the headspace above the aqueous reaction mixture. The concentration of tungsten ion per 100 ml is 80 ppm.

After 10 minutes, the test strip is removed and within the next 2 minutes, the pad color is visually compared with the 481396 color chart. The result is about 100 ppb As.

This result demonstrates the usefulness of a mixture of zinc dust, an alkali metal tungstate and more than 50 wt. % sodium chloride.

EXAMPLE 3

Reagent 3: A mixture of 62 g Oxone® powder and 290 g of malic acid is prepared. Reagent T1 is a mixture of zinc powder and sodium tungstate, and corresponds to Reagent T1 of Example 1.

Following the procedure of Example 1 including the analysis of a sample containing 5 ppb As, 1.93 g of Reagent 3 and 0.84 g of Reagent T1 (first run, mixture stored with desiccant; second run, mixture stored without desiccant) are used. The results (two runs) are 5 ppb and 5 ppb As, respectively. Usefulness of a mixture of malic acid and Oxone® is demonstrated.

Stability of Reagent 3 is analyzed as follows:

1.12 g of Reagent 3 is dissolved in 50 ml of deionized water (resulting solution pH 2.1), and a sample of the resulting solution is evaluated using a commercially available DPD-3 test strip and Micro 20 meter. Conversion of KI to iodine is determined from the solution color, and the average reading (3 readings) is 135 ppm.

More than one year later, 1.13 g of Reagent 3 is dissolved in 50 ml of water and evaluated using the same method. The average reading (5 readings; combination of test strip and Micro 20) is 133 ppm. Stability of a mixture of malic acid and Oxone® for more than one year is demonstrated.

EXAMPLE 4

Reagent 4: A mixture of 62 g Oxone® powder and 290 g of citric acid is prepared. Reagent T1 is a mixture of zinc powder and sodium tungstate, and corresponds to Reagent T1 of Example 1.

Following the procedure of Example 1 including the analysis of a sample containing 5 ppb As, 1.95 g of Reagent 4 and 0.84 g of Reagent T1 (first run, mixture stored with desiccant; second run, mixture stored without desiccant) are used. The results (two runs) are 5 ppb and 5 ppb As, respectively. Usefulness of a mixture of citric acid and Oxone® is demonstrated.

EXAMPLE 5

Reagent 1 is a mixture of Oxone® powder and L-tartaric acid, and corresponds to Reagent 1 of Example 1.

Reagent M1: A mixture of 106.6 g zinc powder and 40 g potassium molybdate is prepared. Thereafter, a portion of M1 is stored with desiccant, and a portion is stored without desiccant. The ratio of potassium molybdate to zinc powder is about 1:2.7.

Following the procedure of Example 1 including the analysis of a sample containing 5 ppb As, 2.57 g of Reagent 1 and 0.84 g of Reagent M1 (first nm, mixture stored with desiccant; second run, mixture stored without desiccant) are used. The concentration of molybdenum ion per 100 ml is 922 ppm. The results (two runs) are 5 ppb and 5 ppb As, respectively. Usefulness of a mixture of zinc powder and an alkali metal molybdate is demonstrated.

EXAMPLE 6

Reagent 3 is a mixture of Oxone® powder and malic acid, and corresponds to Reagent 3 of Example 3.

Reagent M1 is a mixture of zinc powder and potassium molybdate, and corresponds to Reagent M1 of Example 5.

Following the procedure of Example 1 including the analysis of a sample containing 5 ppb As, 1.93 g of Reagent 1 and 0.84 g of Reagent M1 (first run, mixture stored with desiccant; second run, mixture stored without desiccant) are used. The results (two runs) are 3-4 ppb and 3-4 ppb As, respectively. These results indicate that the combination of Reagents 3 and M1 may not be as good as the reagent combination of Example 3.

EXAMPLE 7

Reagent 4 is a mixture of Oxone® powder and citric acid, and corresponds to Reagent 4 of Example 4.

Reagent M1 is a mixture of zinc powder and potassium molybdate, and corresponds to Reagent M1 of Example 5.

Following the procedure of Example 1 including the analysis of a sample containing 5 ppb As, 1.95 g of Reagent 1 and 0.84 g of Reagent M1 (first run, mixture stored with desiccant; second run, mixture stored without desiccant) are used. The results (two runs) are 5 ppb and 5-6 ppb As, respectively. These results demonstrate the usefulness of the combination of Reagents 4 and M1.

EXAMPLE 8

Reagent 5: A mixture of 62 g Oxone® powder and 290 g of succinic acid is prepared.

Reagent T1 is a mixture of zinc powder and sodium tungstate, and corresponds to Reagent T1 of Example 1.

100 ml of an aqueous solution (deionized water) containing 100 ppb arsenic, instead of 5 ppb arsenic, is added to a 160 ml reaction bottle. Thereafter, following the procedure of Example 1, 2.7 g of Reagent 5 and 0.84 g of Reagent T1 are used. The pad color is visually compared with a commercially available color chart (Industrial Test Systems, Inc., Method 481396 color chart). The result is 100 ppb As. This result demonstrates the usefulness of a mixture of succinic acid and Oxone®.

Evaluation of Stability and Removal of Sulfide Interference

About 5 months later, reagent 5 is evaluated for removal of sulfide interference. 2.7 g of Reagent 5 is added to 100 ml of deionized water containing 5.4 ppm sulfide ion, but 0 ppb arsenic. Concentration of sulfide ion is confirmed using Micro 20 meter sulfide procedure. The procedure of Example 1 is followed, and the pad color is visually evaluated to determine removal of sulfide interference using the 481396 color chart. The result is 0 ppb As. This result demonstrates the stability of a mixture of succinic acid and Oxone® for about 5 months, and the effectiveness of the mixture in removing sulfide interference.

EXAMPLE 9

Reagent 1A is a mixture of Oxone® powder and L-tartaric acid, and corresponds to Reagent 1A of Example 1.

Reagent M2: A mixture of 45 g zinc dust, 1.5 g potassium molybdate and 53.7 g sodium chloride is prepared. The ratio of potassium molybdate to zinc dust is 1:30.

The procedure of Example 2 is followed including use of a sample containing 100 ppb arsenic, except that 2.7 g of Reagent 1A is used with 0.65 g of Reagent M2. The concentration of molybdenum ion per 100 ml is 52 ppm. The pad color is visually compared with the 481396 color chart. The result is about 100 ppb As. This result demonstrates the usefulness of a mixture of zinc dust, an alkali metal molybdate, and more than 50 wt. % sodium chloride.

EXAMPLE 10

Reagent 6: A mixture of 2.5 g potassium permanganate powder and 97.5 g of L-tartaric acid is prepared.

Reagent T1 is a mixture of zinc powder and sodium tungstate, and corresponds to Reagent T1 of Example 1.

(a) 100 ml of deionized water containing 0 ppb arsenic and 4 ppm sulfide ion, is added to a 160 ml reaction bottle. Concentration of sulfide ion is confirmed using Micro 20 meter sulfide procedure. 2.7 g of Reagent 6 is added to the aqueous solution, and the mixture is capped, shaken vigorously for 15 seconds, and then the uncapped bottle is allowed to stand undisturbed for 2 minutes. Thereafter, 0.84 g of Reagent T1 is added, and the mixture is capped and shaken vigorously for 5 seconds, and then the reaction bottle is closed using a cap that has a slit opening and holds a test strip pad carrying mercuric bromide indicator in the headspace above the aqueous reaction mixture. After 10 minutes, the test strip is removed and within the next 2 minutes, the pad color is determined visually using the Method 481396 color chart. The result is 0 ppb As, and appears to demonstrate the removal of sulfide interference.

(b) The procedure of paragraph (a) is repeated except that the aqueous solution contains 100 ppb arsenic in addition to 4 ppm sulfide ion. The pad color is compared with the Method 481396 color chart, and the result is more than 200 ppb but less than 250 ppb arsenic.

(c) The procedure of paragraph (a) is repeated except that the aqueous solution contains 100 ppb arsenic but no sulfide ion. The result is more than 200 ppb but less than 250 ppb arsenic.

Evaluation of Stability and Removal of Sulfide Interference

About 4 months later, reagent 6 is re-evaluated for removal of sulfide interference. 100 ml of deionized water containing 0 ppb arsenic and 4.25 ppm sulfide ion, is added to a 160 ml reaction bottle. Concentration of sulfide ion is confirmed using Micro 20 meter sulfide procedure. The foregoing procedure of this Example is followed, which includes using 2.7 g of Reagent 6 and 0.84 g of Reagent T1. The pad color is visually evaluated to determine removal of sulfide interference using the 481396 color chart. The result is approximately 0 ppb As, and demonstrates stability of reagent 6 and the removal of sulfide interference.

EXAMPLE 11

Reagent 6A: A mixture of 0.5 g potassium permanganate powder and 99.5 g of L-tartaric acid is prepared.

Reagent T2 is a mixture of zinc dust, sodium tungstate anhydrous and sodium chloride, and corresponds to Reagent T2 of Example 2.

The procedure of Example 2 is followed including use of a sample containing 100 ppb As, except that 2.8 g of Reagent 6A is used with 0.65 g of Reagent T2. The pad color is visually evaluated using the 481396 color chart. The result is more than 100 ppb but less than 150 ppb As.

The procedure of Example 2 is again followed, except that 2.8 g of Reagent 6A is used with 0.65 g of Reagent T2, and except that the sample contains 10 ppb As instead of 100 ppb As. The pad color is visually evaluated using the 481396 color chart. The result is approximately 10 ppb As.

The procedure of Example 2 is again followed, except that 2.8 g of Reagent 6A is used with 0.65 g of Reagent T2, and except that the sample contains 500 ppb As instead of 100 ppb As. The pad color is visually evaluated using the 481396 color chart. The result is approximately 500 ppb As.

These results demonstrate the usefulness of Reagent 6A.

EXAMPLE 12

Reagent 6A is a mixture of potassium permanganate powder and L-tartaric acid, and corresponds to Reagent 6A of Example 11.

Reagent T1 is a mixture of zinc powder and sodium tungstate, and corresponds to Reagent T1 of Example 1.

Reagent 6A when used with Reagent T1, is evaluated for removal of sulfide interference. 100 ml of deionized water containing 100 ppb arsenic and 5.1 ppm sulfide ion, is added to a 160 ml reaction bottle. Concentration of sulfide ion is confirmed using Micro 20 meter sulfide procedure. The procedure of Example 2 is followed including use of a sample containing 100 ppb arsenic, except that 2.8 g of Reagent 6A is used with 0.84 g of Reagent T1. The pad color is visually evaluated using the 481396 color chart. The result is about 200 ppb As.

100 ml of deionized water containing 0 ppb arsenic and 5.1 ppm sulfide ion, is added to a 160 ml reaction bottle. Concentration of sulfide ion is confirmed using Micro 20 meter sulfide procedure. The procedure of Example 2 is again followed, except that 2.8 g of Reagent 6A is used with 0.84 g of Reagent T1, and except that the sample contains 0 ppb As instead of 100 ppb As. The pad color is visually evaluated using the 481396 color chart. The result is approximately 0 ppb As.

The removal of sulfide interference by Reagent 6A appears to be demonstrated.

EXAMPLE 13

Reagent 6A is a mixture of potassium permanganate powder and L-tartaric acid, and corresponds to Reagent 6A of Example 11.

Reagent M2 is a mixture of zinc dust, potassium molybdate and sodium chloride, and corresponds to Reagent M2 of Example 9.

The procedure of Example 2 is followed including use of a sample containing 100 ppb arsenic, except that 2.8 g of Reagent 6A is used with 0.65 g of Reagent M2. The pad color is visually evaluated using the 481396 color chart. The result is more than 100 ppb but less than 150 ppb As.

The procedure of Example 2 is again followed, except that 2.8 g of Reagent 6A is used with 0.65 g of Reagent M2, and except that the sample contains 10 ppb As instead of 100 ppb As. The pad color is visually evaluated using the 481396 color chart. The result is approximately 10 ppb As.

The procedure of Example 2 is again followed, except that 2.8 g of Reagent 6A is used with 0.65 g of Reagent M2, and except that the sample contains 500 ppb As instead of 100 ppb As. The pad color is visually evaluated using the 481396 color chart. The result is more than 500 ppb but less than 600 ppb As.

This result and that of Example 11 demonstrate the usefulness of Reagent 6A with an alkali metal tungstate or molybdate as an additive.

EXAMPLE 14

Reagent 7: A mixture of 1.5 g potassium permanganate powder and 98.5 g of L-tartaric acid is prepared.

Reagent T1 is a mixture of zinc powder and sodium tungstate, and corresponds to Reagent T1 of Example 1.

(a) 100 ml of deionized water containing 0 ppb arsenic and 5-6 ppm sulfide ion, is added to a 160 ml reaction bottle. Concentration of sulfide ion is confirmed using Micro 20 meter sulfide procedure. The procedure of Example 10 is followed, except that 2.7 g of Reagent 7 is used with 0.84 g of Reagent T1. The pad color is visually evaluated for the removal of sulfide interference using the 481396 color chart. The result is approximately 0 ppb As. This result appears to demonstrate the removal of sulfide interference.

(b) The procedure of paragraph (a) is repeated except that the sample contains 100 ppb arsenic in addition to 5 to 6 ppm sulfide ion. The pad color is visually evaluated using the 481396 color chart. The result is approximately 400 ppb As.

(c) The procedure of paragraph (a) is repeated except that that the sample contains 100 ppb arsenic but no sulfide ion. The pad color is visually evaluated using the 481396 color chart. The result is approximately 400 ppb As.

The results of paragraphs (b) and (c) indicate that a lower concentration of zinc and/or sodium tungstate may be beneficial. This is indicated by comparison with the results of Example 11, which uses reagent T2.

COMPARATIVE EXAMPLE 1

Reagent 8: A mixture of 2.5 g potassium permanganate powder and 97.5 g of malonic acid is prepared.

Reagent T1 is a mixture of zinc powder and sodium tungstate, and corresponds to Reagent T1 of Example 1.

(a) 100 ml of deionized water containing 0 ppb arsenic and 4 ppm sulfide ion, is added to a 160 ml reaction bottle. Concentration of sulfide ion is confirmed using Micro 20 meter sulfide procedure. The procedure of Example 10 is followed, except that 2.7 g of Reagent 8 is used with 0.84 g of Reagent T1. The pad color is determined visually using the Method 481396 color chart, and also using an uncalibrated electronic meter. The result of both determinations is 0 ppb As.

(b) The procedure of paragraph (a) is repeated except that the aqueous solution contains 100 ppb arsenic in addition to 4 ppm sulfide ion. The visually determined result is more than 100 ppb but less than 150 ppb arsenic.

(c) The procedure of paragraph (a) is repeated except that that the aqueous solution contains 100 ppb arsenic but no sulfide ion. The visually determined result is more than 100 ppb but less than 150 ppb arsenic.

These results appear to indicate the usefulness of Reagent 8.

Evaluation of Stability of Reagent 8

About 3½ months later, Reagent 8 is re-evaluated for removal of sulfide interference, using a procedure similar to that of Example 10(a). 100 ml of deionized water containing 0 ppb arsenic and 4.25 ppm sulfide ion, is added to a 160 ml reaction bottle. Concentration of sulfide ion is confirmed using Micro 20 meter sulfide procedure. 2.7 g of Reagent 8 is added to the aqueous solution, and the mixture is capped, shaken vigorously for 15 seconds, and then the capped bottle is allowed to stand undisturbed for 2 minutes. Thereafter, 0.84 g of Reagent T1 is added, and the mixture is capped and shaken vigorously for 5 seconds, and then the reaction bottle is closed using a cap that has a slit opening and holds a test strip pad carrying mercuric bromide indicator. After 10 minutes, the test strip is removed and within the next 2 minutes, the pad color is determined visually using the Method 481396 color chart. The result is approximately 200 ppb As. Comparison to the results of paragraph (a) of this Comparative Example 1 indicates instability of reagent 8 for arsenic analysis.

EXAMPLE 15

Reagent 9: A mixture of 17.6 g of Oxone® powder and 82.3 g of L-tartaric acid and 0.1 g iron(II) sulfate is prepared.

Reagent T1 is a mixture of zinc powder and sodium tungstate, and corresponds to Reagent T1 of Example 1.

(a) 100 ml of deionized water containing 0 ppb arsenic and 4.5 ppm sulfide ion, is added to a 160 ml reaction bottle. Concentration of sulfide ion is confirmed using Micro 20 meter sulfide procedure. The procedure of Example 10 is followed, except that 2.7 g of Reagent 9 is used with 0.84 g of Reagent T1. The concentration of Fe(II) per 100 ml is 10 ppm. The pad color is determined visually using the Method 481396 color chart. The result is 0 ppb As.

(b) The procedure of paragraph (a) is repeated except that the aqueous solution contains 100 ppb arsenic in addition to 4.5 ppm sulfide ion. The visually determined result is more than 100 ppb but less than 150 ppb arsenic.

(c) The procedure of paragraph (a) is repeated except that that the aqueous solution contains 100 ppb arsenic but no sulfide ion. The visually determined result is approximately 150 ppb arsenic.

Similar results are obtained using the foregoing combination for Reagent 9, except 1.0 g iron(II) sulfate and 81.4 g of the acid, and except using a concentration of 6.8 ppm sulfide ion, with the results respectively being 0 ppb As, more than 100 ppb but less than 150 ppb As, and more than 100 ppb but less than 150 ppb As.

These results indicate the usefulness of Reagent 9, including enhanced sulfide removal using Fe(II).

Stability of Reagent 9 and the removal of sulfide interference are evaluated about 4 months later, following the procedure of paragraph (a) of this Example, except that the aqueous solution contains 2.1 ppm of sulfide ion. The result is 0 ppb As. This result indicates usefulness, enhanced removal of sulfide interference using Fe(II), and stability of Reagent 9 for 4 months.

EXAMPLE 16

Reagent 10: A mixture of 17.6 g of Oxone® powder and 82.3 g of malic acid and 0.1 g iron(II) sulfate is prepared.

Reagent T1 is a mixture of zinc powder and sodium tungstate, and corresponds to Reagent T1 of Example 1.

Over 3 months after preparation of Reagent 10, usefulness, stability and the removal of sulfide interference are evaluated as follows: 100 ml of deionized water containing 0 ppb arsenic and 0.4 ppm sulfide ion, is added to a 160 ml reaction bottle. Concentration of sulfide ion is confirmed using Micro 20 meter sulfide procedure. The procedure of Example 10 is followed, except that 2.7 g of Reagent 10 is used with 0.84 g of Reagent T1. The concentration of Fe(II) per 100 ml is 10 ppm. The pad color is determined visually using the Method 481396 color chart. The result is 0 ppb As.

By comparison, for a 100 ml of an aqueous solution (deionized water) containing 0 ppb arsenic and 0.5 ppm sulfide ion, the result for a like Reagent 10 composition without Fe(II), is about 5 ppb As.

These results indicate usefulness, enhanced removal of sulfide interference using Fe(II), and also stability of Reagent 10 for more than 3 months.

EXAMPLE 17

Reagent 11: A mixture of 17.7 g of Oxone® powder and 82.5 g of citric acid and 0.1 g iron(II) sulfate is prepared.

Reagent T1 is a mixture of zinc powder and sodium tungstate, and corresponds to Reagent T1 of Example 1.

Over 3 months after preparation of Reagent 11, usefulness, stability and the removal of sulfide interference are evaluated as follows: 100 ml of deionized water containing 0 ppb arsenic and 4 ppm sulfide ion, is added to a 160 ml reaction bottle. Concentration of sulfide ion is confirmed using Micro 20 meter sulfide procedure. The procedure of Example 10 is followed, except that 2.7 g of Reagent 10 is used with 0.84 g of Reagent T1. The concentration of Fe(II) per 100 ml is 10 ppm. The pad color is determined visually using the Method 481396 color chart. The result is 0 ppb As.

By comparison, for a 100 ml of deionized water containing 0 ppb arsenic and 0.5 ppm sulfide ion, the result for a like Reagent 11 composition without Fe(II), is less than 5 ppm As.

These results indicate usefulness, enhanced removal of sulfide interference using Fe(II), and stability of Reagent 11 for more than 3 months.

COMPARATIVE EXAMPLE 2

Reagent 12: A mixture of 17.6 g of Oxone® powder and 82.3 g of tartaric acid and 0.1 g copper (II) sulfate is prepared.

Reagent T1 is a mixture of zinc powder and sodium tungstate, and corresponds to Reagent T1 of Example 1.

(a) 100 ml of deionized water containing 0 ppb arsenic and 1.76 ppm sulfide ion, is added to a 160 ml reaction bottle. Concentration of sulfide ion is confirmed using Micro 20 meter sulfide procedure. The procedure of Example 10 is followed, except that 2.7 g of Reagent 12 is used with 0.84 g of Reagent T1. The concentration of copper ion per 100 ml is 11 ppm. The pad color is determined visually using the Method 481396 color chart. The result is 0 ppb As.

(b) The procedure of paragraph (a) is repeated except that the deionized water contains 100 ppb arsenic in addition to 1.76 ppm sulfide ion. The visually determined result is 10 ppb As, which indicates Cu(II) should not be included in a combination of an oxidizing agent and tartaric acid.

COMPARATIVE EXAMPLE 3

Reagent 13: A mixture of 17.6 g of Oxone® powder and 82.3 g of tartaric acid and 0.1 g nickel (II) sulfate is prepared.

Reagent T1 is a mixture of zinc powder and sodium tungstate, and corresponds to Reagent T1 of Example 1.

(a) 100 ml of deionized water containing 0 ppb arsenic and 1.22 ppm sulfide ion, is added to a 160 ml reaction bottle. Concentration of sulfide ion is confirmed using Micro 20 meter sulfide procedure. The procedure of Example 10 is followed, except that 2.7 g of Reagent 13 is used with 0.84 g of Reagent T1. The concentration of nickel ion per 100 ml is 10 ppm. The pad color is determined visually using the Method 481396 color chart. The result is 0 ppb As.

(b) The procedure of paragraph (a) is repeated except that the deionized water contains 100 ppb arsenic in addition to 1.22 ppm sulfide ion. The visually determined result is 20 ppb As, which indicates Ni(II) should not be included in a combination of an oxidizing agent and tartaric acid.

COMPARATIVE EXAMPLE 4

Reagent 14: A mixture of 17.6 g of Oxone® powder and 82.3 g of tartaric acid and 0.1 g tin (II) chloride is prepared.

Reagent T1 is a mixture of zinc powder and sodium tungstate, and corresponds to Reagent T1 of Example 1.

(a) 100 ml of deionized water containing 0 ppb arsenic and 1.22 ppm sulfide ion, is added to a 160 ml reaction bottle. Concentration of sulfide ion is confirmed using Micro 20 meter sulfide procedure. The procedure of Example 10 is followed, except that 2.7 g of Reagent 14 is used with 0.84 g of Reagent T1. The concentration of tin ion per 100 ml is 17 ppm. The pad color is determined visually using the Method 481396 color chart. The result is 5 ppb As. This result indicates that this concentration of tin chloride is not effective in enhancing the removal of sulfide interference.

(b) The procedure of paragraph (a) is repeated except that the deionized water contains 100 ppb arsenic in addition to 1.22 ppm sulfide ion. The visually determined result is 40 ppb As, which indicates Sn(II) should not be included in a combination of an oxidizing agent and tartaric acid.

A reagent mixture of Oxone® powder and maleic acid, a carboxylic acid that includes a C—C double bond, is found to be not useful for the arsenic analysis. By comparison, useful carboxylic acids are free of a C—C double bond.

The present invention may be carried out with various modifications without departing from the spirit or essential attributes thereof, and accordingly, reference should be made to the appended claims, rather than to the foregoing specification as indicating the scope of the invention.

The invention claimed is:

1. A reagent system for inorganic arsenic analysis in an acidic aqueous reaction environment that eliminates interference of an otherwise interfering oxidizable substance, wherein inorganic arsenic is reduced to arsine gas in the course of an arsenic reduction reaction, and said arsenic reduction reaction is in the presence of an effective amount of an agent for increasing the rate of the arsine gas production, said reagent system comprising a first reagent mixture in particulate form comprising (a) at least one useful non-corrosive type acidifying agent containing a carboxylic acid moiety, wherein said at least one useful non-corrosive type acidifying agent is a di- or tri-carboxylic acid and includes a C—C moiety between carboxyl acid groups, and (b) an oxidizing agent in an amount effective to eliminate interference of an otherwise interfering oxidizable substance, wherein said oxidizing agent comprises an alkali metal permanganate salt, and about 0.3 to 5 wt. % of said alkali metal permanganate salt is used in said first reagent mixture, and a second reagent mixture in particulate form, that comprises (a) an effective amount of an inorganic arsenic reducing agent in particulate form, said inorganic arsenic reducing agent comprising zinc, and (b) at least one additive that during said arsenic reduction reaction, functions as, or from which is generated, said agent for increasing the rate of the arsine gas production, wherein said at least one additive is a transition metal compound selected from iron, cobalt, nickel, copper, tin, tungsten and molybdenum compounds, and combinations thereof.

2. The reagent system of claim 1, wherein said at least one useful non-corrosive type acidifying agent is selected from tartaric acid, malic acid, citric acid, succinic acid, and combinations thereof.

3. The reagent system of claim 1, wherein said transition metal compound in said second reagent mixture is an Fe(II) compound.

4. The reagent system of claim 1, wherein the amount of said at least one useful non-corrosive type acidifying agent in said first reagent mixture is greater than the amount of the oxidizing agent.

5. The reagent system of claim 1, wherein the amount of said arsenic reducing agent in said second reagent mixture is greater than the amount of said at least one additive.

6. The reagent system of claim 1, wherein said second reagent mixture further comprises more than 50 wt. % of an alkali metal halide.

7. The reagent system of claim 6, wherein said alkali metal halide is sodium chloride.

8. The reagent system of claim 1, wherein said at least one useful non-corrosive type acidifying agent is tartaric acid.

9. The reagent system of claim 1, wherein said reagent system further comprises a test strip bearing an indicator for arsine gas for analysis of inorganic arsenic.

10. The reagent system of claim 1, wherein said agent for increasing the rate of the arsine gas production is a divalent transition metal cation or a transition metal cation of greater valence than divalent.

11. The reagent system of claim 1, wherein said second reagent mixture further comprises an alkali metal halide and is free flowing.

12. The reagent system of claim 1, wherein said transition metal compound in said second reagent mixture is a tungsten compound.

13. The reagent system of claim 12, wherein said second reagent mixture further comprises sodium chloride.

\* \* \* \* \*